US006893027B2

(12) United States Patent
Burdette

(10) Patent No.: US 6,893,027 B2
(45) Date of Patent: May 17, 2005

(54) SURGICAL CHUCK KEY

(75) Inventor: Charles H. Burdette, Woodruff, SC (US)

(73) Assignee: Burmon, Inc., Woodruff, SC (US)

( * ) Notice: Subject to any disclaimer, the term of this patent is extended or adjusted under 35 U.S.C. 154(b) by 138 days.

(21) Appl. No.: 10/603,911

(22) Filed: Jun. 25, 2003

(65) Prior Publication Data

US 2004/0201184 A1 Oct. 14, 2004

Related U.S. Application Data

(60) Provisional application No. 60/461,093, filed on Apr. 8, 2003.

(51) Int. Cl.[7] .............................................. B23B 31/06
(52) U.S. Cl. ......................................... 279/147; 81/16
(58) Field of Search ................................ 279/147, 148, 279/150; 81/16, 460, 461; 606/80, 87, 96, 104

(56) References Cited

U.S. PATENT DOCUMENTS

| | | | | |
|---|---|---|---|---|
| 2,012,147 A | * | 8/1935 | Stoner | 81/16 |
| 2,800,936 A | * | 7/1957 | West | 81/460 |
| 3,044,790 A | * | 7/1962 | Stoner | 279/61 |
| 3,686,985 A | * | 8/1972 | Ostrager | 81/16 |
| 4,395,171 A | | 7/1983 | Röhm | 408/241 R |
| 4,467,677 A | | 8/1984 | Grifford | 81/439 |
| 4,997,194 A | | 3/1991 | Krohn | 279/1 K |
| D322,740 S | | 12/1991 | McCart | D8/21 |
| 5,069,585 A | | 12/1991 | Wenz, Jr. | 408/241 R |
| 5,451,067 A | | 9/1995 | Pieper | 279/149 |
| 6,340,163 B1 | | 1/2002 | Newman | 279/147 |
| 6,488,288 B2 | | 12/2002 | Tally | 279/147 |

FOREIGN PATENT DOCUMENTS

| GB | 2055062 A | * | 2/1981 | ........... B23B/31/06 |
|---|---|---|---|---|
| GB | 2171342 A | * | 8/1986 | ............ B25D/5/00 |

* cited by examiner

Primary Examiner—Daniel W. Howell
Assistant Examiner—Michael W. Talbot
(74) Attorney, Agent, or Firm—Howard & Howard

(57) ABSTRACT

A surgical drill chuck key comprising an elongated body of a cylindrical construction having a smooth rounded surface. A key gear located at a first distal end of the elongated body having a plurality of gear teeth with radiused knuckles. A handle having an elongated shaft being constructed and arranged so that no sharp edges are provided on the handle. The elongated shaft having a curved J-shape wherein a first portion of the elongated shaft is directed back towards the elongated body in a generally parallel arrangement to a second portion of the elongated shaft extending radially outward from the elongated body so that the first portion and the second portion of the elongated shaft cooperate to provide a thumb grip for increased leverage when turning the key. The elongated body, gear teeth, and handle being finished through an abrasive bead blasting process to round off all edges and surfaces.

33 Claims, 5 Drawing Sheets

SURGICAL CHUCK KEY

CROSS REFERENCE TO RELATED APPLICATION

Applicant claims priority of U.S. Provisional Patent Application No. 60/461,093, filed Apr. 8, 2003.

FIELD OF THE INVENTION

The present invention relates to chuck keys for operating the jaws of a drill chuck to hold a tool implement, and more particularly, to a surgical chuck key adapted for use in surgical procedures to operate a drill chuck without snagging and tearing, or puncturing a surgical latex glove.

BACKGROUND OF THE INVENTION

The prior art is replete with various types of chuck keys covering a range of shapes, sizes and specified benefits. However, no attention has been paid to chuck keys specifically for use in surgical procedures with a drill chuck of the type having a rotatable sleeve with a plurality of sleeve gear teeth for cooperating with the key. The problem with drill chuck keys currently being used in surgical procedures is that the keys have sharp edges that snag and tear surgical latex gloves. Additionally, the chuck keys currently being used in surgical procedures have small handles for turning the key, which makes it difficult to apply proper torque to the drill chuck. The small handle in turn causes the surgeon to press harder to apply the proper torque, often puncturing the surgeon's latex glove. Additionally, the handle itself typically has relatively sharp edges at the ends which easily puncture the latex gloves when being handled by the surgeon. Once the surgeon's glove is punctured, he must leave the operating room, rescrub, get new gloves, and then return to surgery. This is time a surgeon typically does not have to waist during a procedure.

For example, U.S. Pat. No. 5,069,585 discloses a drill chuck key having an elongated smooth cylindrical body with an enlarged toothed head disposed at a first distal end, and a T-handle mounted at the opposite distal end. The teeth of the toothed head are arched from the pilot pin at the front of the key to the base of the toothed head, which presents a sharp circumferential edge that may easily tear a surgeon's latex gloves. Additionally, the ends of the handle, where the greatest pressure is applied to the user's gloves, also are shown having a relatively sharp, non-radiused edge, which easily punctures the latex glove when turning the key. No disclosure is provided for machining and treating the key to round off all the edges and surfaces.

U.S. Pat. No. 6,340,163 discloses a snag-resistant chuck key having an elongated cylindrical handle carrying an angled chuck key at a first distal end and an attachment member at a second distal end for mounting the chuck key to a drill power cord. Again, however, there is no disclosure for treating and machining the surfaces and edges of the key to round off the edges of the teeth, handle, or body of the chuck to ensure there are no sharp surfaces and edges that may cut a latex glove.

U.S. Pat. Nos. 4,467,677 and 6,488,288 disclose multi-ended chuck keys of various designs. However, there is no discussion of treating or machining the keys to round off all the surfaces and edges to prevent damaging a latex glove.

U.S. Pat. No. 4,395,171 discloses a chuck key having a cylindrical body with an array of teeth formed at a front end, and a crosspiece extending diametrically through the body at the opposite end from the teeth. Again, the teeth appear to have sharp corners at intersecting edges and there is no disclosure for treating and machining the keys to round off the corners of the teeth and handle to prevent puncturing a latex glove.

None of the above noted patents address the particular problem faced by surgical teams in the operating room where the chuck keys damage the user's latex gloves because they have sharp edges and teeth.

Accordingly, it is an object of the present invention to provide a surgical chuck key specifically for use in surgical procedures to operate a drill chuck without damaging the surgeon's latex gloves.

It is an object of the present invention to provide a surgical chuck key for use in surgical procedures that has no sharp edges on the body or teeth of the key that may puncture the surgeon's latex gloves.

It is an object of the present invention to provide a surgical chuck key for use in surgical procedures that has a larger handle with no edges adapted for easily applying greater torque to the drill chuck without damaging the surgeon's latex gloves.

It is an object of the present invention to provide a surgical chuck key machined and treated to ensure all surfaces and edges are smooth and rounded to prevent snagging, tearing, or puncturing a latex glove when the key is being handled.

SUMMARY OF THE INVENTION

The above objectives are accomplished according to the present invention by providing a surgical drill chuck key specifically designed for operating a surgical drill chuck during a surgical procedure. Preferably, the key comprises an elongated body of a cylindrical construction having a smooth rounded surface extending generally concentrically along a central axis.

A key gear is located at a first distal end of the elongated body having a plurality of gear teeth being equally spaced around the circumference of the first distal end in a generally concentric manner about the central axis. Each of the gear teeth have a first surface extending radially outward from the central axis in a generally perpendicular manner, a second beveled surface intersecting with the first surface and extending from the first surface at an inclined angle to the central axis, and a third surface intersecting with the second surface and extending from the second surface in a generally parallel arrangement with the central axis of the elongated body so that the third surface is coplanar with and integrally merged with the rounded surface of the elongated body.

A first knuckle is formed at the intersection of the first surface and the second surface having a radiused corner, and a second knuckle is formed at the intersection of the second surface and the third surface having a radiused corner so that no sharp edges are provided on said gear teeth at the intersection of said first, second, and third surfaces.

A handle is generally carried at a second distal end of the elongated body and includes a thumb grip portion of expanded surface area being constructed and arranged with smooth rounded surfaces and no edges that may contact a finger pressing against said thumb grip portion.

Advantageously, the elongated body, gear teeth, and handle are finished to round off all edges and surfaces.

Preferably, the handle has an elongated shaft of smooth cylindrical construction extending generally perpendicular to the central axis in a radial direction outward from the elongated body. The elongated shaft includes a first convex rounded end and a second convex rounded end so that no edges are provided on the handle. Advantageously, the elongated shaft has a curved J-shape wherein a first portion of the elongated shaft is directed back towards the elongated body in a generally parallel arrangement to a second portion of the elongated shaft extending radially outward from the elongated body so that the first portion and the second portion of the elongated shaft cooperate to provide the thumb grip for increased leverage when turning the key.

The second distal end of the elongated body has a convex rounded end forming a portion of the smooth rounded surface of the elongated body to prevent snagging and tearing of surgical latex gloves.

A pilot is carried generally concentrically at the first distal end for engaging a pilot hole of the surgical drill chuck. The pilot has a radiused edge on the distal end of the pilot which engages the pilot hole to prevent snagging and tearing of surgical latex gloves.

In a further advantageous embodiment, the elongated body includes an identification groove recessed around the circumference of the elongated body reducing the diameter of the elongated body along a portion of the length of the elongated body. The identification groove is representative of a specific size of the key gear teeth for cooperating with a specific size of drill chuck. The identification groove includes a first radiused shoulder and a second radiused shoulder extending upward from the groove and integrally merging in a common plane with the smooth rounded surface of the elongated body so that there are no sharp edges associated with the identification groove. The identification groove is disposed on the elongated body immediately adjacent the key gear at the first distal end. The first radiused shoulder of the identification groove integrally merges with the third surface of the key gear teeth to be coplanar with the smooth rounded surface of the elongated body.

In an alternative embodiment, the second distal end of the elongated body includes a secondary key gear. The secondary key gear is adapted for cooperating with a different size drill chuck than the key gear included at the first distal end. The secondary key gear includes a plurality of secondary gear teeth constructed and arranged as described above for the key gear teeth of the first distal end so that no sharp edges are provided on the secondary key gear teeth.

In this alternative embodiment, the second distal end includes a secondary pilot carried generally concentrically about the central axis for engaging a pilot hole of the drill chuck. The secondary pilot has a radiused edge on the distal end of the secondary pilot that engages the pilot hole to prevent snagging and tearing of surgical latex gloves. Additionally, the handle is disposed generally between the first distal end and the second distal end.

Advantageously, the elongated body, gear teeth, and handle are finished through an abrasive bead blasting process to remove all burs formed during machining of the key and to round off all edges and surfaces to prevent damaging a surgical latex glove during handling and use. The abrasive bead blasting process provides a glare reducing matte finish on the handle, elongated body, and key gear teeth, making it easier for the surgeon to operate with.

Accordingly, a surgical drill chuck key is provided with smooth rounded surfaces to prevent snagging, puncturing, and tearing surgical latex gloves during surgical operations.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DETAILED DESCRIPTION OF A PREFERRED EMBODIMENT

Figure 1:
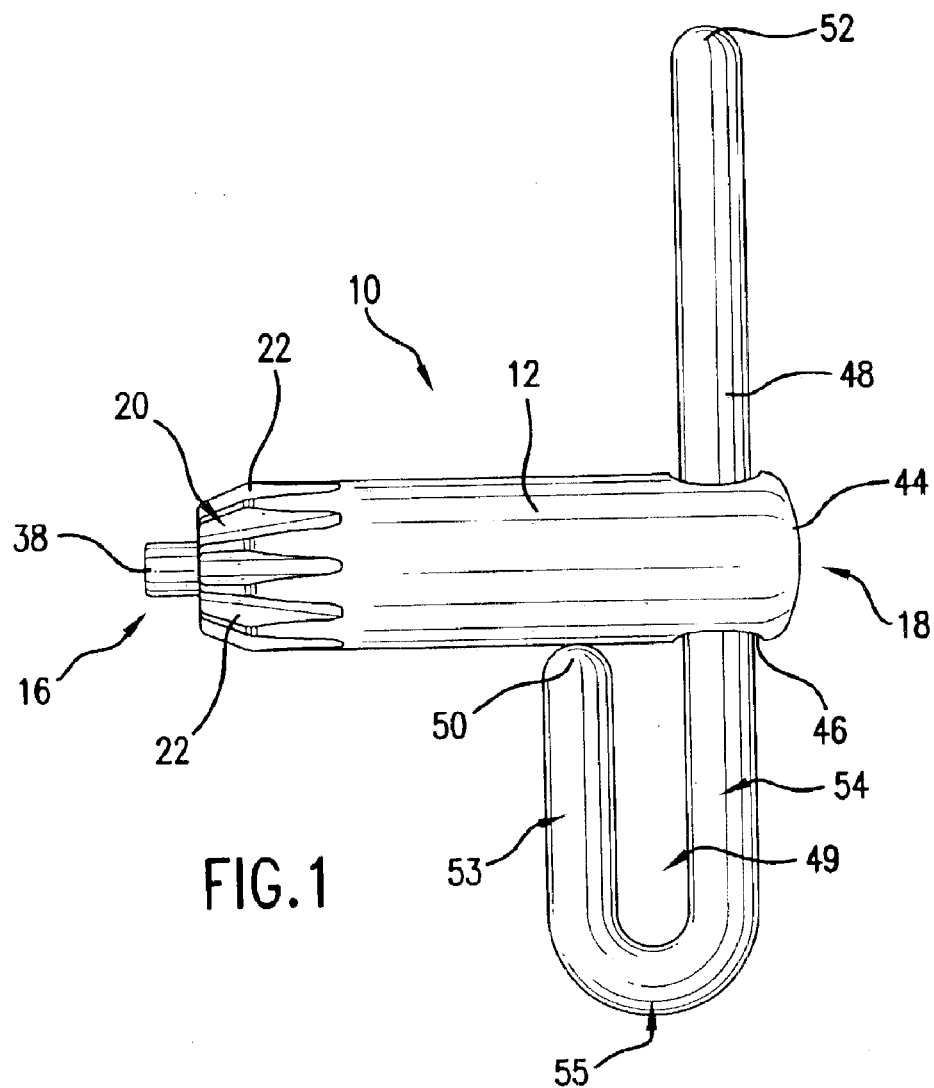
FIG. 1 shows a side view of the chuck key according to the invention.

With reference to the drawings, the invention will now be described in more detail. Referring to FIG. 1, a surgical drill chuck key, designated generally as 10, is shown for use in surgical procedures with a drill chuck of the type having jaws for holding a tool implement, and a rotatable sleeve operatively associated with the jaws having a plurality of sleeve gear teeth for cooperating with the key to open and close the jaws to receive and hold tool implements. Advantageously, the surgical drill chuck key is machined and finished to provide smooth rounded edges as surfaces on all parts of the key, as well as to remove any burs which may damage a surgical latex glove during handling and use of the key.

Figure 2A:
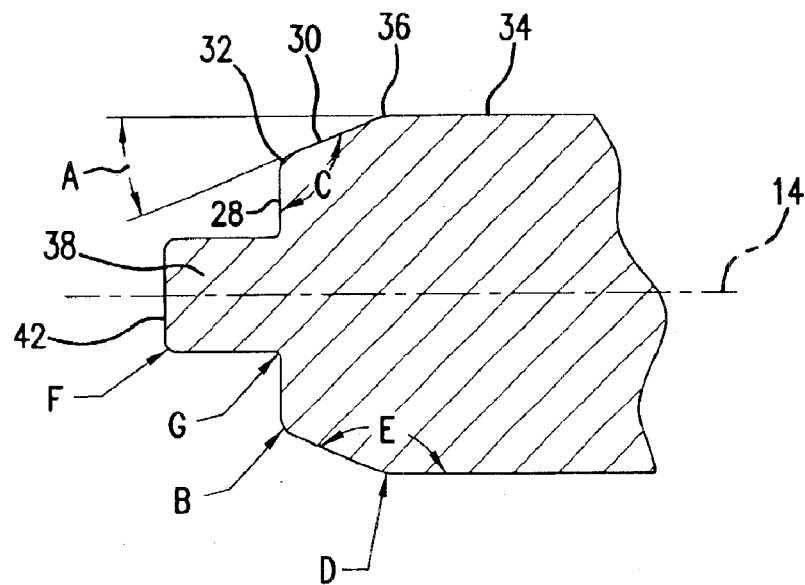
FIG. 2a shows a cross-section view of the gear teeth according to the invention.
Figure 2B:
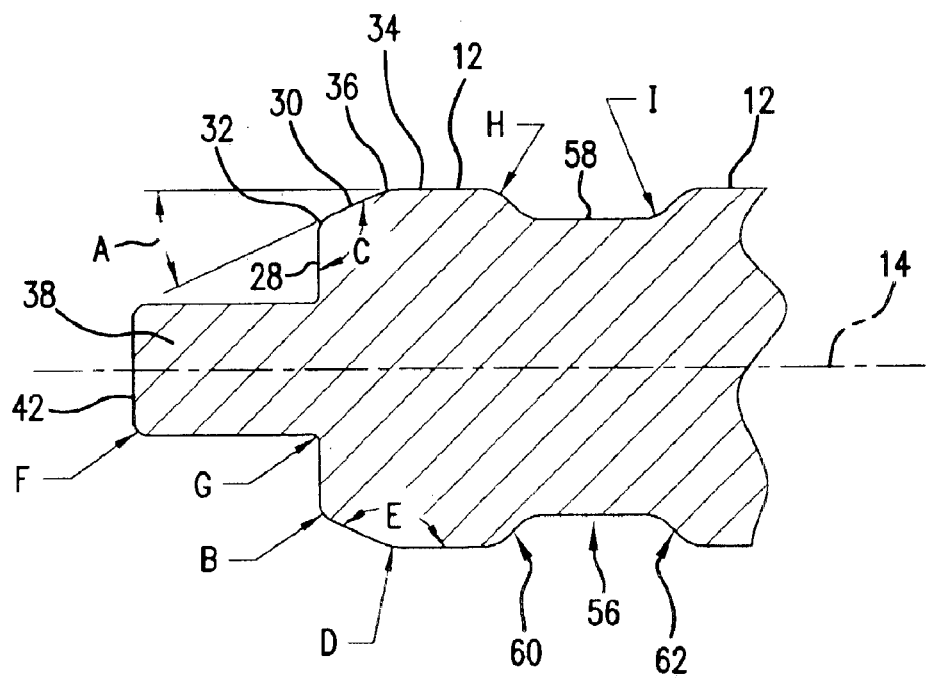
FIG. 2b shows a cross-section view of the gear teeth of an alternative embodiment having an identification groove according to the invention.

The key comprises an elongated body 12 extending concentrically along a central axis 14 (FIGS. 2a and 2b). Elongated body 12 preferably has a cylindrical construction with a smooth rounded outer surface. Elongated body 12 is machined to include a key gear, designated generally as 20, at a first distal end 16 of the cylindrical body. Key gear 20 has a plurality of key gear teeth 22 being equally spaced circumferentially around first distal end 16 in a generally concentric manner about central axis 14. Key gear teeth 22 are constructed and arranged to engage and cooperate with the sleeve gear teeth of the drill chuck. Key gear teeth 22 cooperate with the sleeve gear teeth to rotate the rotatable sleeve of the drill chuck to open and close the jaws to receive and hold tool implements.

Figure 1A:
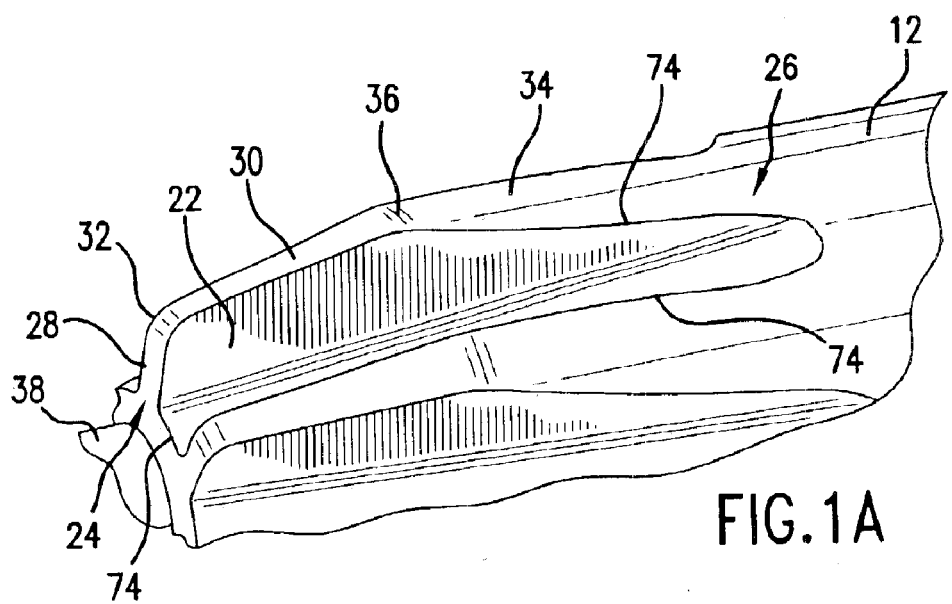
FIG. 1a shows a perspective view of the gear teeth according to the invention.

Referring to FIGS. 1a, 2a, and 2b, key gear teeth 22 have a front tooth end, designated generally as 24, and a rear tooth end, designated generally as 26. Each of the gear teeth is formed having a first surface 28 extending radially outward from. central axis 14 in a generally perpendicular manner. First surface 28 may be angled inward toward elongated body 12 a maximum of 3° to promote cooperation with complementary sleeve gear teeth on the drill chuck. A second beveled surface 30 intersects with first surface 28 and extends from the first surface at an inclined angle, designated generally as A, to central axis 14. Angle A of second beveled surface 30 may be constructed so as to extend upward from first surface 30 at any angle between 10° and 45° in relation to central axis 14. Preferably, second surface 30 is beveled at an angle of 23° to promote blunt rounded knuckles at intersecting surfaces, as described below. A third surface 34 intersects with second surface 30 and extends from the second surface in a generally parallel arrangement with central axis 14 of elongated body 12. Third surface 34 is constructed and arranged so that third surface 34 of each of the gear teeth is coplanar with and integrally merged with the rounded outer surface of cylindrical elongated body 12 at rear tooth end 26. Gear teeth 22 are preferably formed by carving the teeth into elongated body 12 so that third surface 34 is derived from the surface of the elongated body and therefore precisely integrated with the elongated body without an edge being provided at rear end 26 of the teeth that may snag, tear or puncture a surgical latex glove while handling the key to operate the drill chuck.

As noted above, a first knuckle 32 is formed at the intersection of first surface 28 and second surface 30. First knuckle 32 is radiused, designated generally by radius B, to provide a smooth rounded corner to prevent damaging a surgical latex glove. Depending on the size of the chuck the key is adapted for, radius B may vary between 0.01" and 0.05", with the preferred embodiment of the key having a radius B of 0.03". Corresponding to any variation in angle of second beveled surface 30, interior angle C between first surface 28 and second beveled surface 30 can vary between 100° and 135°. However, to provide the most advantageous blunt knuckles at the intersection between first surface 28 and second surface 30, the preferred embodiment of the key is constructed and arranged to have an interior angle C of approximately 113°. Additionally, a second knuckle 36 is formed at the intersection of second surface 30 and third surface 34. As with first knuckle 32, second knuckle 36 is also radiused, designated generally by radius D, to provide a smooth rounded corner to prevent damaging a surgical latex glove. Again, depending on the size of the chuck the key is adapted for, radius D may typically vary between 0.01" and 0.05", with the preferred embodiment of the key having a radius D of 0.04". Corresponding to any variation in angle of second beveled surface 30, interior angle E between second surface 30 and third surface 34 can vary between 135° and 170°. However, to provide the most advantageous blunt knuckles at the intersection between second surface 30 and third surface 34, the preferred embodiment of the key is constructed and arranged to have an interior angle E of 157°. As a result, utilizing the angles and radiuses of the preferred embodiment, a surgical drill chuck key is provided with no sharp edges on the gear teeth at the intersections of first surface 28, second surface 30, and third surface 34, while also providing gentle rounded corners that do not snag, tear, or puncture latex gloves through normal handling of the key.

A pilot 38 is included at first distal end 16 carried generally concentrically for engaging a pilot hole of the drill chuck to align and hold key gear teeth 22 in engagement with the sleeve gear teeth of the chuck. Pilot 38 has a smooth radiused edge, designated generally as F, on distal end 42 of the pilot that engages the pilot hole. Radiused edge F is provided to prevent snagging and tearing of surgical latex gloves while manipulating the key. Additionally, radiused edge G is provided at the intersection of pilot 38 and first surface 28 to help prevent burs from forming on the drill chuck or key during use, as well as to add to the overall rounded nature of all intersecting surfaces on the key. Advantageously, key gear teeth 22 and pilot 38 are machined to be concentric within 0.005 total indicated run-out from central axis 14.

Referring to FIG. 1, elongated body 12 includes a second distal end, designated generally as 18, constructed and arranged to include a convex rounded end 44 forming a portion of the smooth rounded surface of elongated body 12 to prevent snagging and tearing of surgical latex gloves. Slot 46 is formed generally though second distal end 18 for carrying a handle 48 to turn the key when engaging the drill chuck.

Handle 48 is carried generally at second distal end 18 for increased leverage in applying torque to the key. Handle 48 is constructed and arranged to include an expanded surface area, designated generally as 49, which provides a thumb grip portion for increased leverage when turning the key. Irrespective of the shape of the expanded surface area of the handle, the thumb grip portion must be constructed and arranged so that no sharp edges come into contact with the finger pressing against the expanded surface area.

In the preferred embodiment, handle 48 comprises an elongated shaft of smooth cylindrical construction extending generally perpendicular to central axis 14 in a radial direction outward from elongated body 12. The elongated shaft of handle 48 includes a first convex rounded end 50 and a second convex rounded end 52 so that no edges are provided on the handle that may snag, tear, or puncture a surgical latex glove. Advantageously, the elongated shaft has a curved J-shape wherein a first portion, designated generally as 53, of the elongated shaft is directed back towards elongated body 12 in a generally parallel arrangement to a second portion, designated generally as 54, of the elongated shaft which extends radially outward from elongated body 12. First portion 53 and second portion 54 are interconnected by radiused curve portion, designated generally as 55, of the elongated shaft to eliminate any edges and sharp surfaces. As such, first portion 53 and second portion 54 cooperate with radiused curve portion 55 to provide expanded surface area 49, which acts as a thumb grip for increased leverage when turning the key. The surface of handle 48 is milled and finished to be smooth, as with elongated body 12, to prevent damaging the latex gloves during use. Additionally, the elongated shaft of handle 48 is constructed and arranged to include a larger diameter than typical chuck keys used for non-surgical purposes. Preferably, the elongated shaft has a diameter of approximately 0.187", which provides a more ergonomic handle that results in increased leverage to apply torque to the drill chuck sleeve, while at the same time ensuring that no damage is done to the latex gloves of the user.

Figure 3:
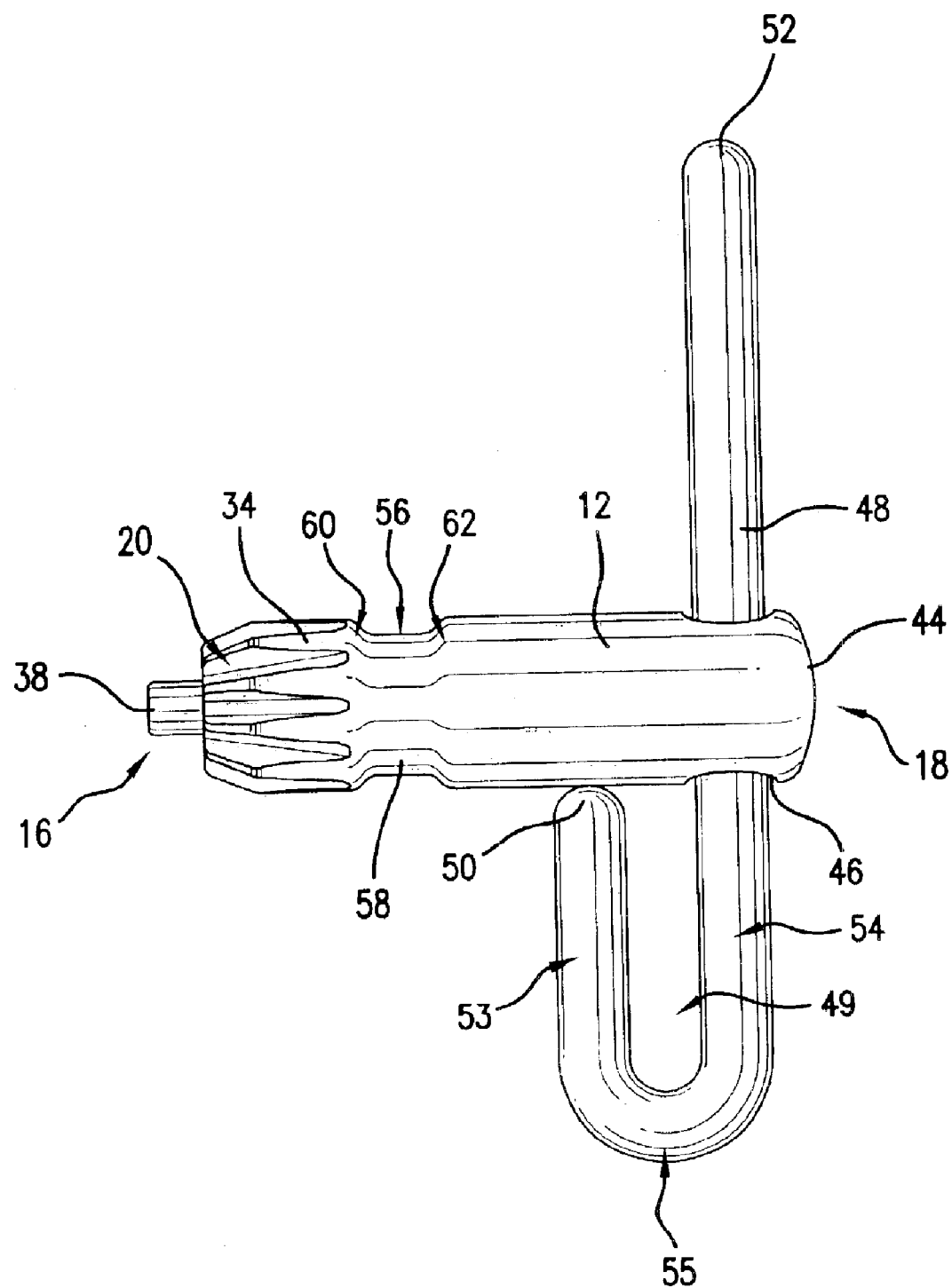
FIG. 3 shows a side view of a chuck key having an identification groove according to the invention.

Referring to FIGS. 2b and 3, in an alternative embodiment, elongated body 12 includes an identification groove, designated generally as 56. Identification groove 56 is representative of a specified size of surgical drill chuck key for cooperating with a specific size of drill chuck so that the correct key for a specific size of drill chuck can be easily identified on a tray of tools during surgery. Identification groove 56 includes recessed elongated body surface 58 being recessed circumferentially around elongated body 12 and reducing the diameter of the elongated body along a portion of the length of the elongated body. A first radiused shoulder, designated generally as 60, and a second radiused shoulder, designated generally as 62, extend upward from recessed elongated body surface 58 and integrally merge into a common plane with the smooth rounded outer surface of elongated body 12 so that there are no sharp edges associated with the identification groove, which allows a latex glove to run directly over the grove without snagging, tearing, or puncturing the glove. As best shown in FIG. 2, a concave radiused corner, designated generally as radius I, is provided at the intersection of recessed elongated body surface 58 and first and second radiused shoulder 60 and 62, respectively. Concave radiused corner I eliminates any corner that might otherwise pinch and snag a latex glove that may come into contact with the area around and including recessed elongated body surface 58. Additionally, a convex radiused corner, designated generally as H, is also provided at the intersection of elongated body surface 12 and first and second radiused shoulder 60 and 62, respectively. Convex radiused corner H eliminates any sharp edge on the portion of the identification groove most likely to be contact by the surgeon's latex gloves when handling the key.

In the alternative embodiment shown in FIG. 3, identification groove 56 is formed on the elongated body immediately adjacent key gear 20 at first distal end 16. To eliminate any rough or sharp edges, first radiused shoulder 60 integrally merges with third surface 34 of key gear teeth 22 to be coplanar with the smooth rounded surface 12 of the elongated body.

Figure 4:
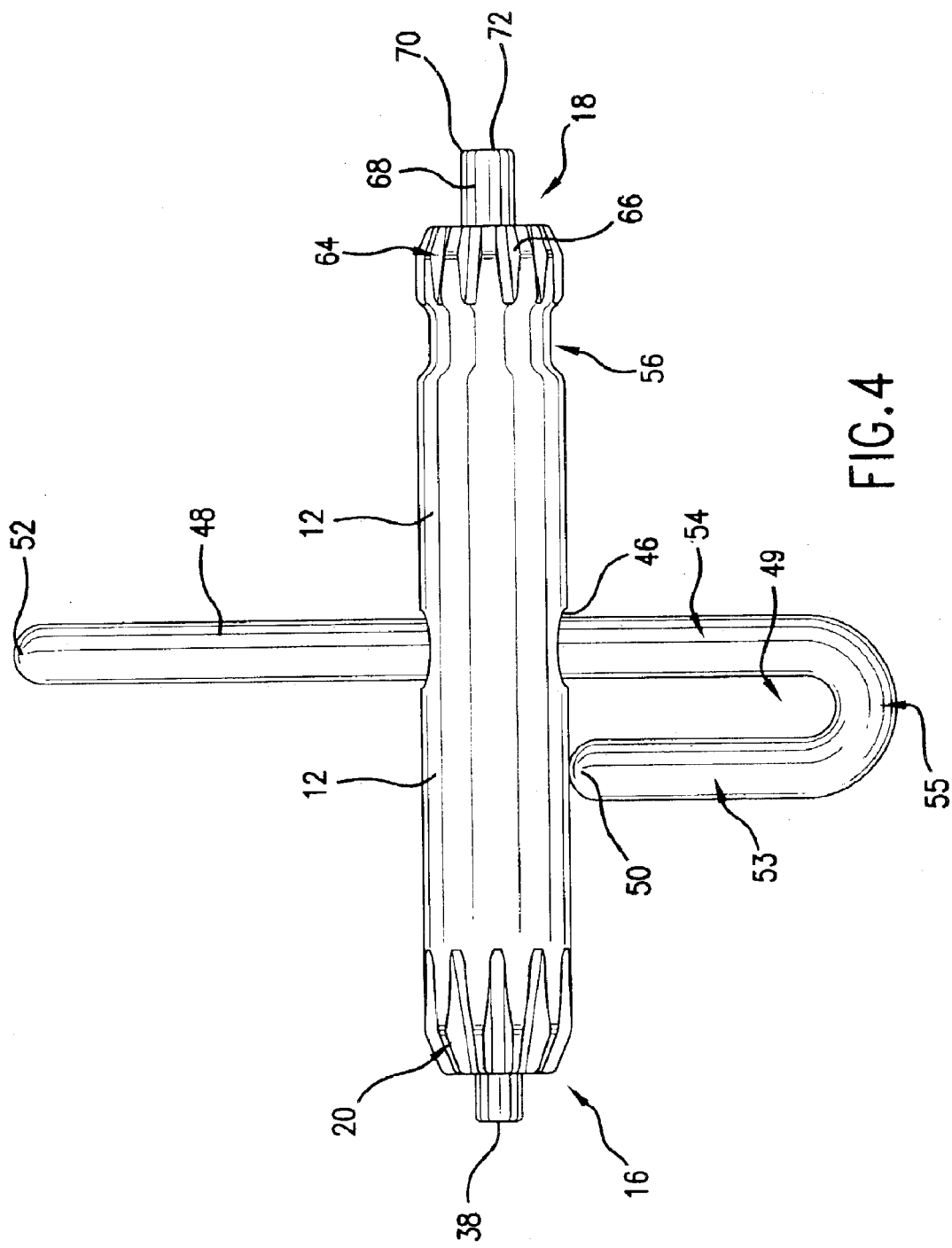
FIG. 4 shows an alternative duel-ended embodiment of the chuck key wherein each end includes a key gear adapted to work with a different sized chuck; and, FIG. 5 shows a chuck key being finished according to the invention.

Referring to FIG. 4, in a further advantageous embodiment, elongated body 12 is adapted to include a secondary key gear, designated generally as 64, at second distal end 18. Secondary key gear 64 is adapted for cooperating with a different size drill chuck than key gear 20 included at first distal end 16. Secondary key gear 64 includes a plurality of secondary key gear teeth 66 equally spaced circumferentially around second distal end 18 in a generally concentric manner about central axis 14 (FIG. 2). Secondary key gear teeth 66 are formed as disclosed above for key gear teeth 22. Accordingly, secondary key gear teeth 66 are constructed and arranged to include the various radiuses and angles described for key gear teeth 22 so that smooth radiused knuckles having a gentle curvature at the intersections of the first, second and third tooth surfaces are provided to prevent damage to latex gloves when handling the key. Also, the third surface is again constructed and arranged to be coplanar with the smooth rounded outer surface of elongated body 12 so that no edges are formed at the intersection of the teeth and the elongated body to prevent snagging and tearing of surgical latex gloves. Second distal end 18 also includes a secondary pilot 68 for engaging the pilot hole of the drill chuck. As with pilot 38, secondary pilot 68 has a smooth radiused edge 70 on distal end 72 of the secondary pilot, which has radius F (FIG. 2b) to prevent snagging and tearing of surgical latex gloves. Preferably, handle 48 is disposed generally at a central position between first distal end 16 and second distal end 18. Additionally, identification groove 56 is disposed generally at second distal end 18 to distinguish between key gear 20 and secondary key gear 64 to easily indicate which end of the key to use for a specific size of chuck.

Figure 5:
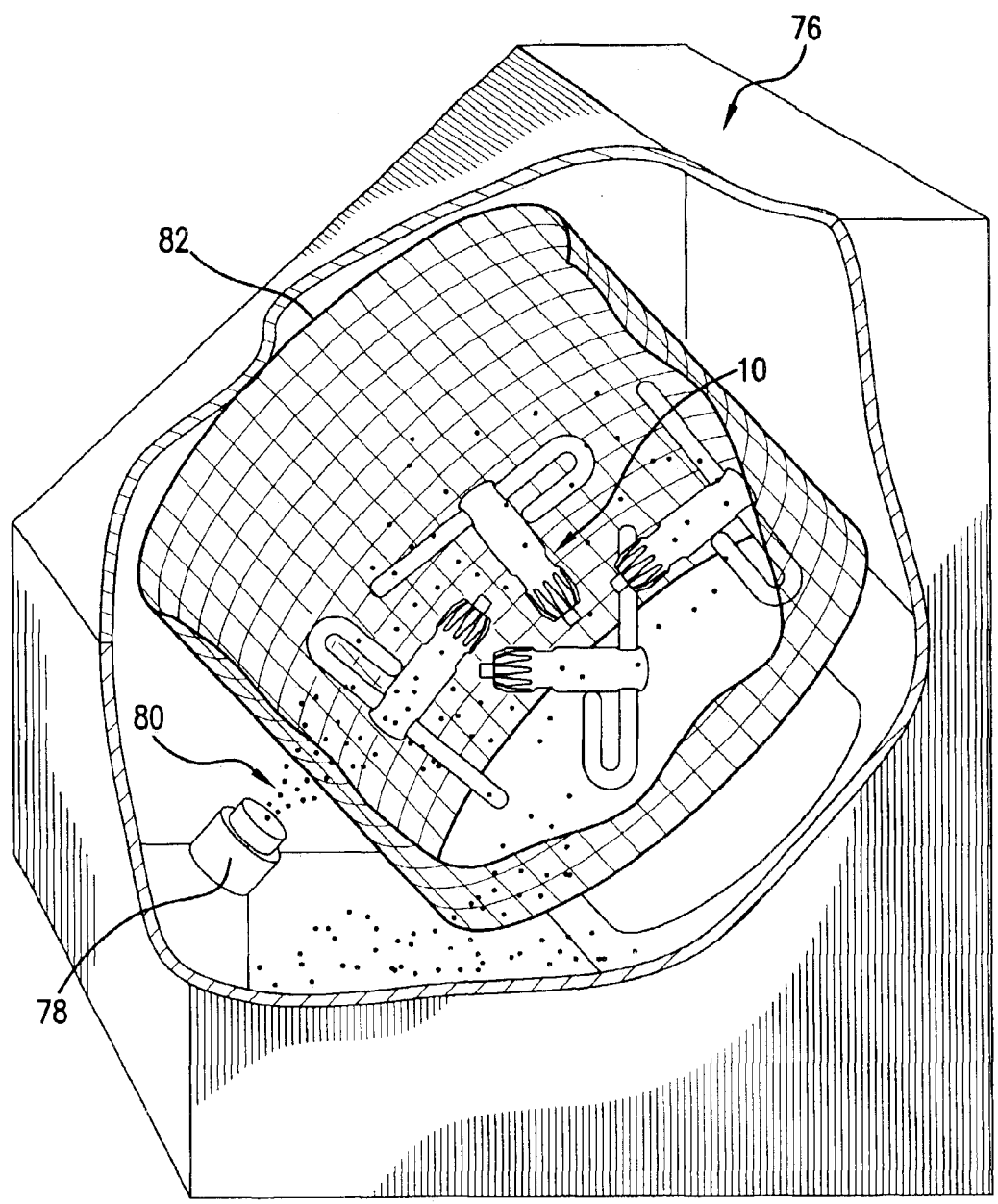

Referring to FIG. 5, advantageously, keys 10 are finished through a bead blasting process, to round off and dull all the surfaces and edges of the key gear teeth, handle, and elongated body. The process removes any burs formed during machining so that the key is smooth to the touch to prevent snagging, tearing or puncturing a surgical latex glove. The process ensures that the corners of intersecting tooth surfaces such as inner teeth edges 74 (FIG. 1a), are significantly dulled down and rounded to provide a radiused edge that will not damage a latex glove. As a result, a surgical drill chuck key is provided with smooth rounded surfaces, not only on the handle and body, but on the gear teeth in order to prevent snagging and tearing surgical latex gloves during surgical operations requiring the use of a drill.

As shown in FIG. 5, a bead blasting unit, designated generally as 76, is shown having a spray nozzle 78 for spraying glass beads 80 at extremely high pressure into a rotating basket 82 holding a plurality of keys 10. Preferably, the keys are finished by bead blasting the keys for a period of 10 minutes, or more as necessary, in the rotating basket to ensure that every side of the keys are treated by the glass beads to be smooth, dull, and rounded. Advantageously, the bead blasting treatment results in a matte finish on the keys, which eliminates glare from the bright lights in the operating room. Alternatively, the keys may be finished through polishing or chemical treatments that are sufficiently abrasive to remove any burs and produce the desired dulling effect on the edges and surfaces of the elongated body, key gear, and handle.

While a preferred embodiment of the invention has been described using specific terms and dimensions necessary to a proper understanding of the features of the invention, such description is only for illustrative purposes of a preferred embodiment, and it is to be understood that changes and variations to the preferred embodiment may be made to provide a surgical drill chuck key with rounded surfaces and edges without departing from the spirit or scope of the following claims.

What is claimed is:

1. A surgical drill chuck key for operating a surgical drill chuck during a surgical procedure, said key comprising:
    an elongated body of a cylindrical construction having a smooth rounded surface extending generally concentrically along a central axis;
    a key gear located at a first distal end of said elongated body having a plurality of gear teeth being equally spaced around the circumference of said first distal end in a generally concentric manner about said central axis;
    each of said gear teeth having a first surface extending radially outward from said central axis in a generally perpendicular manner, a second beveled surface intersecting with said first surface and extending from said first surface at an inclined angle to said central axis, and a third surface intersecting with said second surface and extending from said second surface in a generally parallel arrangement with said central axis of said elongated body so that said third surface is coplanar with and integrally merged with said rounded surface of said elongated body;
    a first knuckle formed at the intersection of said first surface and said second surface having a radiused corner, and a second knuckle formed at the intersection of said second surface and said third surface having a radiused corner so that no sharp edges are provided on said gear teeth at the intersection of said first, second, and third surfaces;
    a handle generally carried at a second distal end of said elongated body;
    said handle including a thumb grip portion of expanded surface area being constructed and arranged with smooth rounded surfaces and no edges that may contact a finger pressing against said thumb grip portion; and
    said elongated body, gear teeth, and handle being finished to round off and dull all edges and surfaces;
    whereby a surgical drill chuck key is provided with smooth rounded surfaces to prevent snagging, puncturing, and tearing surgical latex gloves during surgical operations.

2. The chuck key of claim 1 wherein said handle has an elongated shaft of smooth cylindrical construction extending generally perpendicular to said central axis in a radial direction outward from said elongated body.

3. The chuck key of claim 2 wherein said elongated shaft includes a first convex rounded end and a second convex rounded end so that no edges are provided on said handle.

4. The chuck key of claim 3 wherein said elongated shaft has a curved J-shape wherein a first portion of said elongated shaft is directed back towards said elongated body in a generally parallel arrangement to a second portion of said elongated shaft extending radially outward from said elongated body so that said first portion and said second portion of said elongated shaft cooperate to provide said thumb grip for increased leverage when turning said key.

5. The chuck key of claim 1 wherein said second distal end of said elongated body has a convex rounded end forming a portion of said smooth rounded surface of said elongated body to prevent snagging and tearing of surgical latex gloves.

6. The chuck key of claim 1 including a pilot carried generally concentrically at said first distal end for engaging a pilot hole of said surgical drill chuck; said pilot having a radiused edge on the distal end of said pilot which engages said pilot hole to prevent snagging and tearing of surgical latex gloves.

7. The chuck key of claim 1 wherein said elongated body includes an identification groove recessed around the circumference of said elongated body reducing the diameter of said elongated body along a portion of the length of said elongated body; said identification groove being representative of a specific size of said key gear teeth for cooperating with a specific size of drill chuck.

8. The chuck key of claim 7 wherein said identification groove includes a first radiused shoulder and a second radiused shoulder extending upward from a recessed elongated body surface and integrally merging in a common plane with said smooth rounded surface of said elongated body so that there are no sharp edges associated with said identification groove.

9. The chuck key of claim 8 wherein said identification groove is disposed on said elongated body immediately adjacent said key gear at said first distal end; said first radiused shoulder of said identification groove integrally merging with said third surface of said key gear teeth to be coplanar with said smooth rounded surface of said elongated body.

10. The chuck key of claim 1 wherein said second beveled surface extends from said first surface at an inclined angle of between 10° and 45° in relation to said central axis.

11. The chuck key of claim 10 wherein said first knuckle has a radiused corner of between 0.01" and 0.05" with an interior angle between said first and second surfaces of between 100° and 135°.

12. The chuck key of claim 11 wherein said second knuckle has a radiused corner of between 0.01" and 0.05" with an interior angle between said second and third surfaces of between 135° and 170°.

13. The chuck key of claim 1 wherein said second distal end of said elongated body includes a secondary key gear having a plurality of secondary gear teeth equally spaced circumferentially around said second distal end in a generally concentric manner about said central axis; said secondary key gear adapted for cooperating with a different size drill chuck than said key gear included at said first distal end.

14. The chuck key of claim 13 wherein each of said secondary gear teeth having a first surface extending radially outward from said central axis in a generally perpendicular manner, a second beveled surface intersecting with said first surface and extending from said first surface at an inclined angle of between 10° and 45° in relation to said central axis, and a third surface intersecting with said second surface and extending from said second surface in a generally parallel arrangement with said central axis of said elongated body so that said third surface is coplanar with and integrally merged with said rounded surface of said elongated body.

15. The chuck key of claim 14 including a first knuckle formed at the intersection of said first surface and said second surface having a radiused corner of between 0.01" and 0.05" with an interior angle between said first and second surfaces of between 100° and 135°; and a second knuckle formed at the intersection of said second surface and said third surface having a radiused corner of between 0.01" and 0.05" with an interior angle between said second and third surfaces of between 135° and 170°.

16. The chuck key of claim 13 wherein said second distal end includes a secondary pilot carried generally concentrically about said central axis for engaging a pilot hole of said drill chuck; said secondary pilot having a radiused edge on the distal end of said secondary pilot which engages said pilot hole to prevent snagging and tearing of surgical latex gloves.

17. The chuck key of claim 13 wherein said handle is disposed generally between said first distal end and said second distal end.

18. The chuck key of claim 1 wherein said elongated body, gear teeth, and handle are finished through an abrasive bead blasting process to remove all burs formed during machining of the key and to round off all edges and surfaces to prevent damaging a surgical latex glove during handling and use.

19. The chuck key of claim 18 wherein said abrasive bead blasting process provides a glare reducing matte finish on said handle, elongated body, and key gear teeth.

20. A surgical drill chuck key for operating a surgical drill chuck during a surgical procedure, said key comprising:
    an elongated body of a cylindrical construction having a smooth rounded surface extending generally concentrically along a central axis;
    a key gear located at a first distal end of said elongated body having a plurality of gear teeth being equally spaced around the circumference of said first distal end in a generally concentric manner about said central axis;
    a handle generally carried at a second distal end of said elongated body;
    said handle having an elongated shaft of smooth cylindrical construction extending generally perpendicular to said central axis in a radial direction outward from said elongated body;
    said elongated shaft includes a first convex rounded end and a second convex rounded end so that no edges are provided on said handle;
    said elongated shaft having a curved J-shape wherein a first portion of said elongated shaft is directed back towards said elongated body in a generally parallel arrangement to a second portion of said elongated shaft extending radially outward from said elongated body so that said first portion and said second portion of said elongated shaft cooperate to provide a thumb grip for increased leverage when turning said key; and,
    said elongated body, gear teeth, and handle being finished to round off all edges and surfaces;
    whereby a surgical drill chuck key is provided with smooth rounded surfaces to prevent snagging, puncturing, and tearing surgical latex gloves during surgical operations.

21. The chuck key of claim 20 wherein each of said gear teeth have a first surface extending radially outward from said central axis in a generally perpendicular manner, a second beveled surface intersecting with said first surface and extending from said first surface at an inclined angle of between 10° and 45° in relation to said central axis, and a third surface intersecting with said second surface and extending from said second surface in a generally parallel arrangement with said central axis of said elongated body so that said third surface is coplanar with and integrally merged with said rounded surface of said elongated body.

22. The chuck key of claim 21 including a first knuckle formed at the intersection of said first surface and said second surface having a radiused corner of between 0.01" and 0.05" with an interior angle between said first and second surfaces of between 100° and 135°; and a second knuckle formed at the intersection of said second surface and said third surface having a radiused corner of between 0.01" and 0.05" with an interior angle between said second and third surfaces of between 135° and 170°.

23. The chuck key of claim 20 wherein said elongated body includes an identification groove recessed around the circumference of said elongated body reducing the diameter of said elongated body along a portion of the length of said elongated body; said identification groove being representative of a specific size of said key gear teeth for cooperating with a specific size of drill chuck.

24. The chuck key of claim 20 wherein said elongated body, gear teeth, and handle are finished through an abrasive bead blasting process to remove all burs formed during machining of the key and to round off all edges and surfaces to prevent damaging a surgical latex glove during handling and use.

25. The chuck key of claim 24 wherein said abrasive bead blasting process provides a glare reducing matte finish on said handle, elongated body, and key gear teeth.

26. A surgical drill chuck key for operating a surgical drill chuck during a surgical procedure, said key comprising:
   an elongated body of a cylindrical construction having a smooth rounded outer surface extending generally concentrically along a central axis;
   a key gear carried at a first distal end of said elongated body having a plurality of gear teeth being equally spaced around the circumference of said first distal end in a generally concentric manner about said central axis;
   each of said gear teeth having a plurality of tooth surfaces with radiused corners provided at the intersection of adjacent tooth surfaces;
   at least one of said tooth surfaces integrally merging in a coplanar arrangement with said rounded outer surface of said elongated body so that no edge is formed at the intersection of said gear teeth and said elongated body;
   a handle generally carried at a second distal end of said elongated body for turning said key; and,
   said elongated body, gear teeth, and handle being finished to dull all edges and surfaces;
   whereby a surgical drill chuck key is provided with smooth rounded surfaces to prevent snagging, puncturing, and tearing surgical latex gloves during surgical operations.

27. The chuck key of claim 26 wherein said handle including an expanded surface area providing a thumb grip portion for increased leverage when turning said key.

28. The chuck key of claim 27 wherein said thumb grip portion of said handle is constructed and arranged so that no sharp edges come into contact with said finger when pressing against said expanded surface area.

29. The chuck key of claim 28 wherein said handle has an elongated shaft of smooth cylindrical construction extending generally perpendicular to said central axis in a radial direction outward from said elongated body.

30. The chuck key of claim 29 wherein said elongated shaft includes a first convex rounded end and a second convex rounded end so that no edges are provided on said handle.

31. The chuck key of claim 30 wherein said elongated shaft has a curved J-shape wherein a first portion of said elongated shaft is directed back towards said elongated body in a generally parallel arrangement to a second portion of said elongated shaft extending radially outward from said elongated body so that said first portion and said second portion of said elongated shaft cooperate to provide said thumb grip for increased leverage when turning said key.

32. The chuck key of claim 26 wherein said elongated body, gear teeth, and handle are finished through an abrasive bead blasting process to remove all burs formed during machining of the key and to round off all edges and surfaces to prevent damaging a surgical latex glove during handling and use.

33. The chuck key of claim 32 wherein said abrasive bead blasting process provides a glare reducing matte finish on said handle, elongated body, and key gear teeth.

* * * * *